(12) United States Patent
Yokoo et al.

(10) Patent No.: US 10,335,263 B2
(45) Date of Patent: Jul. 2, 2019

(54) ORGAN FOR TRANSPLANTATION AND ORGAN STRUCTURE

(71) Applicant: BIOS Co., Ltd., Tokyo (JP)

(72) Inventors: Takashi Yokoo, Tokyo (JP); Eiji Kobayashi, Tokyo (JP); Hiroshi Nagashima, Kawasaki (JP); Hitomi Matsunari, Kawasaki (JP)

(73) Assignee: BIOS CO., LTD., Tokyo (JP)

( * ) Notice: Subject to any disclaimer, the term of this patent is extended or adjusted under 35 U.S.C. 154(b) by 18 days.

(21) Appl. No.: 15/535,682

(22) PCT Filed: Dec. 4, 2015

(86) PCT No.: PCT/JP2015/084216
§ 371 (c)(1),
(2) Date: Jun. 13, 2017

(87) PCT Pub. No.: WO2016/098620
PCT Pub. Date: Jun. 23, 2016

(65) Prior Publication Data
US 2017/0333173 A1    Nov. 23, 2017

(30) Foreign Application Priority Data

Dec. 19, 2014   (JP) ................... 2014-257957

(51) Int. Cl.
*A61F 2/04*    (2013.01)
*A61F 2/02*    (2006.01)
(Continued)

(52) U.S. Cl.
CPC .................. *A61F 2/02* (2013.01); *A61F 2/04* (2013.01); *A61L 27/36* (2013.01);
(Continued)

(58) Field of Classification Search
CPC ............ A61F 5/451; A61F 5/453; A61F 5/455
See application file for complete search history.

(56) References Cited

U.S. PATENT DOCUMENTS 4,228,550 A * 10/1980 Salkind .................. A61F 2/042
623/23.66
6,613,095 B1 * 9/2003 Levin .................. A61M 1/1678
604/29
(Continued)

FOREIGN PATENT DOCUMENTS

EP          2014316 A1    1/2009
JP        2005-511501     4/2005
(Continued)

OTHER PUBLICATIONS

T Kato et al: "Partial Bladder Transplantation with En Bloc Kidney Transplant—The First Case Report of a 'Bladder Patch Technique' in a Human", American Journal of Translantation, vol. 8, No. 5, May 1, 2008, pp. 1060-1063.
(Continued)

*Primary Examiner* — Andrew M Iwamaye
(74) *Attorney, Agent, or Firm* — Knobbe, Martens, Olson & Bear LLP

(57) ABSTRACT

An organ for transplantation having a kidney, a ureter, and a urinary bladder and an organ structure in which a first ureter, a first urinary bladder, a second ureter and a second urinary bladder are sequentially connected to a kidney can produce urine and excrete the produced urine, and thus is useful for transplantation.

15 Claims, 15 Drawing Sheets

(51) Int. Cl.
*A61L 27/36* (2006.01)
*C12N 5/071* (2010.01)
*A61M 1/14* (2006.01)
*A01K 67/027* (2006.01)

(52) U.S. Cl.
CPC ........ *A61L 27/3679* (2013.01); *C12N 5/0684* (2013.01); *A01K 67/0273* (2013.01); *A01K 2207/30* (2013.01); *A01K 2227/105* (2013.01); *A01K 2227/108* (2013.01); *A61F 2/042* (2013.01); *A61F 2002/048* (2013.01); *A61F 2250/0091* (2013.01); *A61L 2430/22* (2013.01); *A61L 2430/26* (2013.01); *A61M 1/14* (2013.01)

(56) References Cited

U.S. PATENT DOCUMENTS

| | | | |
|---|---|---|---|
| 2007/0239107 A1* | 10/2007 | Lundberg | A61J 15/0015 604/96.01 |
| 2009/0304639 A1 | 12/2009 | Yokoo et al. | |
| 2010/0184220 A1 | 7/2010 | Ram-Liebig et al. | |
| 2011/0104656 A1 | 5/2011 | Kobayashi et al. | |
| 2013/0030262 A1* | 1/2013 | Burnett | A61B 5/0215 600/309 |

FOREIGN PATENT DOCUMENTS

| | | |
|---|---|---|
| JP | 2009-528097 A | 8/2009 |
| WO | WO 03/022123 A2 | 3/2003 |
| WO | WO 2004/016276 A1 | 2/2004 |
| WO | WO 2006/117889 A1 | 11/2006 |
| WO | WO 2010/001951 A1 | 1/2010 |

OTHER PUBLICATIONS

Office Action in Korean Patent Application No. 10-2017-7016740, dated Aug. 28, 2018.
Search Report in Eueopean Patent Application No. 15869825.8, dated Sep. 13, 2018.
Eiji Kobayashi et al., "Buta o Riyo shite Hito no Jinzo o Tsukuru",Transplantation Now, 2012, vol. 25, No. 4, pp. 355 to 358.
Masataka Masuda et al., "Doshu Jinzo Ishoku no Jikkenteki Kenkyu Tokuni KoinuJinzo Ishokuhen no Kogensei ni Tsuite", Japanese Society for Artificial OrgansZasshi, 1966, vol. 3, No. 1, pp. 32 to 33.
Takashi Yokoo, "Rinsho Oyo ni Muketa Jinzo Saisei Kenkyu-Dai 58 Kai TheJapanese Society for Dialysis Therapy Kyoiku Koen yori-", Journal of JapaneseSociety for Dialysis Therapy, 2013, vol. 46, No. 11, pp. 1055 to 1060.
Torino, G. et al., Combined Kidney and Vascularized Total BladderTransplantation: Experience in an Animal Model, Transplantation Proceedings, 2013,vol. 45, p. 2765-2768.
Yokoo T., et al., Generation of a transplantable erythropoietin-producer derived fromhuman mesenchymal stem cells, Transplantation, 85(11), 1654-1658, 2008.
Yokoo T., et al., Human mesenchymal stem cells in rodent whole-embryo culture arereprogrammed to contribute to kidney tissues, PNAS, 102(9), 3296-3300, 2005.
International Search Report in International Patent Application No. PCT/JP2015/084216, dated Feb. 16, 2016.

\* cited by examiner

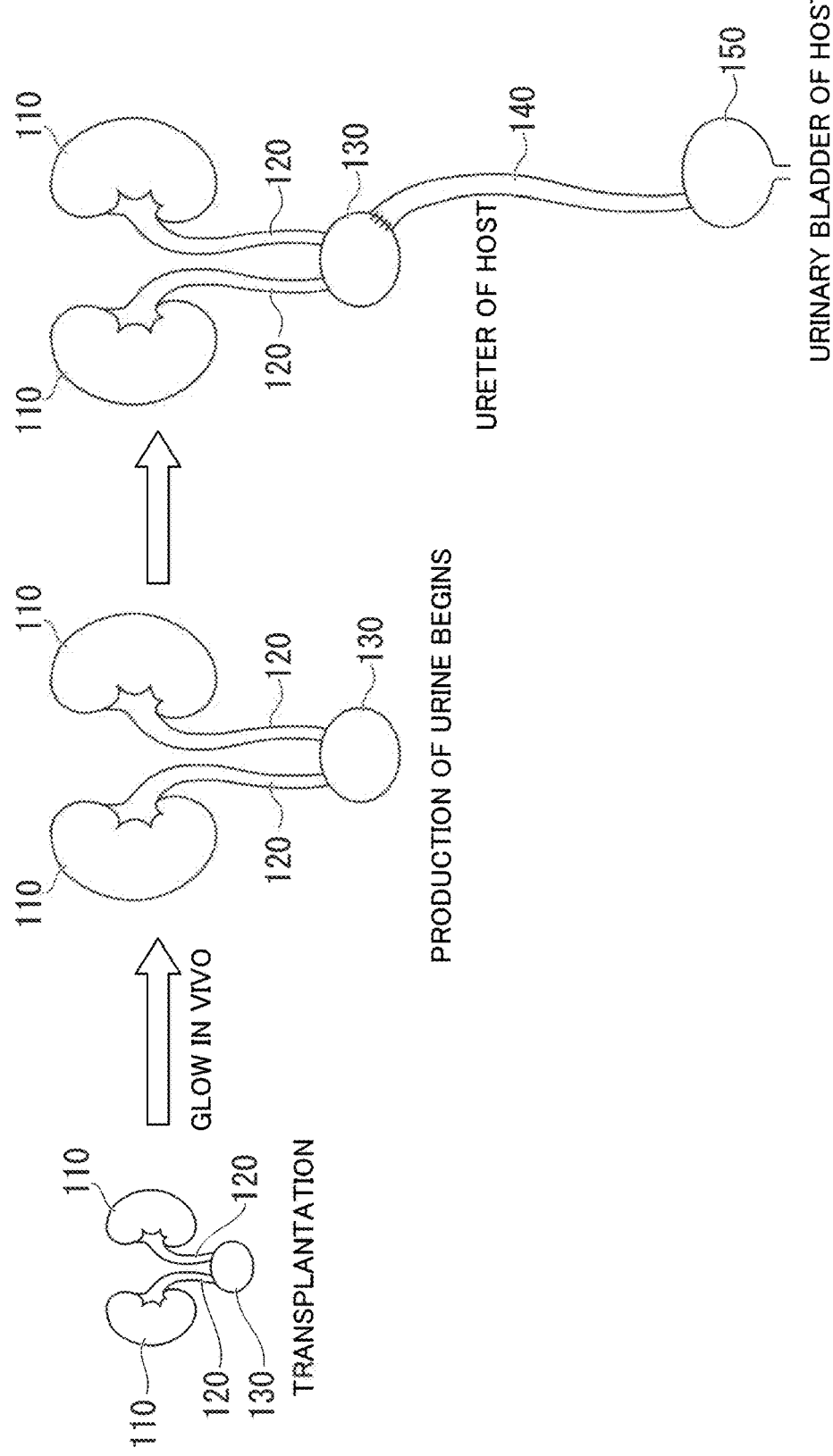

**P<0.0001, *P<0.0005, #P<0.05

ORGAN FOR TRANSPLANTATION AND ORGAN STRUCTURE

TECHNICAL FIELD

The present invention relates to an organ for transplantation and an organ structure. Priority is claimed on Japanese Patent Application No. 2014-257957, filed on Dec. 19, 2014, the content of which is incorporated herein by reference.

BACKGROUND ART

Due to the aging of the population, the expansion of adaptive diseases, etc., artificial dialysis patients are rapidly increasing. Although such patients' lives can be saved by dialysis, artificial dialysis cannot compensate for total kidney function, and therefore patients tend to have an increased risk of cardiovascular disease and increased mortality. Such patients also have great temporal and mental burdens, and in many cases, have difficulty returning to normal social life.

In addition, globally, there are approximately two million patients with end-stage renal failure demanding kidney transplantation, and due to the lack of donor organs, the number of such patients is showing an increase. Accordingly, end-stage renal failure is a serious medical issue.

In light of this, due to recent developments in regenerative medicine, it is becoming possible to form a kidney with the ability to produce urine or erythropoietin from stem cells (refer to Non-Patent Literatures 1 and 2).

CITATION LIST

Non-Patent Literature

[Non-Patent Literature 1]
Yokoo T., et al., Human mesenchymal stem cells in rodent whole-embryo culture are reprogrammed to contribute to kidney tissues, PNAS, 102(9), 3296-3300, 2005
[Non-Patent Literature 2]
Yokoo T., et al., Generation of a transplantable erythropoietin-producer derived from human mesenchymal stem cells, Transplantation, 85(11), 1654-1658, 2008.

SUMMARY OF INVENTION

Technical Problem

However, the inventors realized that even if a regenerated kidney can produce urine, it cannot excrete the produced urine, thereby causing hydronephrosis, and therefore, renal function cannot be maintained for a long time.

For this reason, the present invention is directed to providing an organ for transplantation which is able not only to produce urine, but also to excrete the produced urine. The present invention is also directed to providing an organ structure which is able to produce urine and excrete the produced urine.

Solution to Problem

The present invention is as follows.
(1) An organ for transplantation having a kidney, a ureter and a urinary bladder.
(2) The organ for transplantation described in (1), which is derived from an animal species that is different from a transplantation target.
(3) The organ for transplantation described in (2), wherein the animal is a genetically-manipulated non-human animal.
(4) The organ for transplantation described in (2) or (3), wherein the animal is a pig.
(5) The organ for transplantation described in any one of (1) to (4), which substantially composed of human cells.
(6) The organ for transplantation described in any one of (1) to (5), which is used for transplantation to a human.
(7) The organ for transplantation described in any one of (1) to (5), which is used for transplantation to a cat.
(8) An organ structure in which a kidney, a first ureter, a first urinary bladder, a second ureter and a second urinary bladder are sequentially connected in this order.
(9) The organ structure described in (8), in which an animal species from which the kidney, the first ureter and the first urinary bladder are derived is different from an animal species from which the second ureter and the second urinary bladder are derived.
(10) The organ structure described in (8) or (9), in which the animal from which the kidney, the first ureter and the first urinary bladder are derived is a genetically-manipulated non-human animal.
(11) The organ structure described in any one of (8) to (10), in which the animal from which the kidney, the first ureter and the first urinary bladder are derived is a pig.
(12) The organ structure described in any one of (8) to (11), in which the kidney, the first ureter and the first urinary bladder are substantially composed of human cells.
(13) The organ structure described in any one of (8) to (12), in which the animal from which the second ureter and the second urinary bladder are derived is a human.
(14) The organ structure described in any one of (8) to (12), in which the animal from which the second ureter and the second urinary bladder are derived is a cat.

Advantageous Effects of Invention

According to the present invention, an organ for transplantation which is able not only to produce urine, but also to excrete the produced urine can be provided. In addition, an organ structure which is able to produce urine and also to excrete the produced urine can be provided.

BRIEF DESCRIPTION OF DRAWINGS

FIG. 1 is a diagram illustrating a first embodiment of an organ structure.

DESCRIPTION OF EMBODIMENT

Figure 2A:
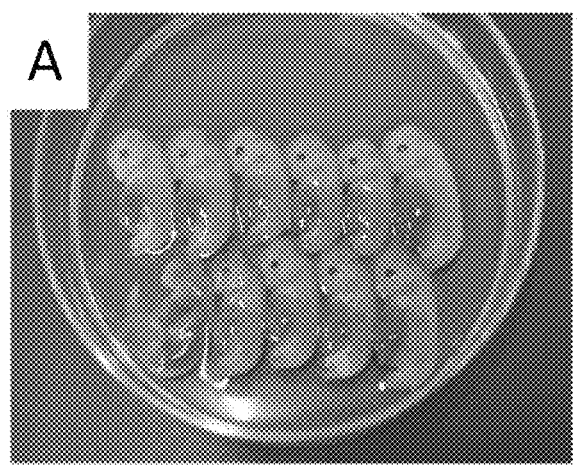
FIG. 2A is an image of cloned porcine fetuses at embryonic day 30.

For example, human bone marrow-derived mesenchymal stem cells may be injected into a kidney-generated site of a growing murine fetus to induce differentiation to a renal lineage in the fetus, and a kidney anlagen may be manufactured.

This kidney anlagen can be extracted right before a vascular aberration phase and transplanted into, for example, the greater omentum, thereby manufacturing a final differentiation-type kidney. In addition, the greater omentum is an apron-like peritoneum that hangs down from the stomach. The transplantation site of a kidney anlagen is not limited to the greater omentum, but may be, for example, the abdominal aorta, or any part in the abdominal cavity.

However, the inventors found that when a regenerated kidney or a heterologous metanephros was transplanted to a living body and grown, although it generated urine, the kidney or metanephros could not excrete the generated urine, hydronephrosis occurred and thus renal function could not be maintained for a long time.

In addition, the inventors found that there was a need for a sustainable excretory drainage of urine using the peristalsis of a ureter to prevent hydronephrosis, and thus completed the present invention.

[Organ for Transplantation]

In a first embodiment, the present invention provides an organ for transplantation which has a kidney, a ureter, and a urinary bladder. In addition, the term "kidney" used herein includes a kidney anlagen such as a metanephros and the like. In addition, the term "urinary bladder" includes an urinary bladder anlagen such as a urodeum and the like.

As will be described later, when only a kidney is transplanted, hydronephrosis and stromal fibrosis progress. On the other hand, when an organ having a kidney, a ureter and a urinary bladder is transplanted, hydronephrosis and stromal fibrosis can be inhibited.

It seems that this is because urine produced by the kidney can be transferred to the urinary bladder due to the peristalsis of the ureter of the organ for transplantation. Conventionally, transplantation of only a regenerated kidney was investigated, but when a regenerated kidney is transplanted with a ureter and a urinary bladder, urine can be produced and then the produced urine can be excreted.

The above-described organ for transplantation may be derived from a type of animal that is different from a transplantation target. For example, a pig-derived organ for transplantation may be transplanted to a human, a cat or the like. This is one of the options that can be made when there is a lack of kidneys for transplantation.

In addition, a cat is one of the most common types of pets, and has a very high morbidity rate of chronic kidney failure. For example, there are reports that approximately 30% of cats die due to chronic kidney failure, and 50% or more of cats die or are euthanized due to a decline in renal function. From these reports, there is a potential demand for kidney transplantation as a life extension technique for cats suffering from kidney diseases.

In the embodiment, the organ for transplantation may be derived from a genetically-manipulated non-human animal which is different from a transplantation target. For example, when being transplanted to a human or a cat, the organ for transplantation may be derived from a pig which is genetically manipulated to reduce rejection. Pigs are suitable for transplantation to humans or the like due to the sizes of their organs, and establishment of their gene manipulation techniques.

In the embodiment, it is preferable that the organ for transplantation to a human is substantially composed of human cells, and it is most preferable that it is composed of a patient's own cells.

Here, the term "substantially" means that addition of cells, other than human cells, will not be excluded when an animal body is used for manufacturing an organ for transplantation. In other words, 90% or more, preferably, 95% or more, and most preferably 99% or more of an organ for transplantation may composed of human cells.

Here, the manufacture of an organ for transplantation will be described. For example, an organ for transplantation can be manufactured by transplanting kidney stem cells derived from pluripotent stem cells such as mammalian-derived mesenchymal stem cells (MSCs), iPS cells or the like to a fetus in a pregnant mammalian host or a fetus separated from a pregnant mammalian host, and differentiating the cells.

By the above-described method, organs for transplantation used for, for example, humans, and pets such as monkeys, cows, sheep, pigs, goats, horses (particularly, racehorses), dogs, cats, rabbits, hamsters, guinea pigs, rats, mice, etc. can be manufactured.

As the host, an ungulate animal such as a cow, a sheep, a pig, a goat, a horse or the like; a mouse; or a genetically manipulated, for example, transgenic, knock-out or knock-in animal listed above is used.

The mesenchymal stem cells or kidney stem cells may be mesenchymal stem cells or kidney stem cells derived from a recipient that is a transplantation target. For example, when the recipient is a human, the mesenchymal stem cells selected from human bone marrow, adipose tissue, circulating blood or umbilical cord blood are used. The mesenchymal stem cells selected from the recipient's own bone marrow, circulating blood or umbilical cord blood may also be used. A selection method is a common surgical technique. The selected cells are preferably subcultured 2 to 5 times under the optimal conditions. In addition, the mesenchymal stem cells may be cultured using a medium kit only for human mesenchymal stem cells, produced by Cambrex BioScience, to inhibit transformation of the mesenchymal stem cells and continue culturing.

A desired gene may be introduced into the mesenchymal stem cells or kidney stem cells using an adenovirus or retrovirus if desired. For example, to assist the kidney formation, a gene may be introduced to express a glial cell line-derived neurotrophic factor (GDNF). This is because the mesenchymal tissue expresses a GDNF right before the kidney is formed, and the first key step for kidney generation is completed by pulling a ureteric bud expressing c-ret, which is a receptor. The inventors identified that due to such transformation, a forming rate of a kidney derived from the injected stem cells increases from $5.0\pm4.2\%$ to $29.8\pm9.2\%$.

Hereinafter, the manufacture of an organ for transplantation to a rat will be exemplified. The mesenchymal stem cells or kidney stem cells are transplanted to a fetus in a pregnant mammalian host. The mesenchymal stem cells or kidney stem cells can be directly transplanted to the fetus in vivo, thereby forming a kidney in the uterus. The transplantation method is a common surgical method, and for example, micro pipettes can be used under ultrasonic diagnostic equipment. The amount of the transplanted cells is, for example, 5 to $1.0\times10^3$. Mesenchymal stem cells can be directly transplanted into an embryo in a large pregnant mammal such as a pig by a transcervical approach, and grown in vivo as they are to be grown into a kidney for transplantation. In addition, the "whole embryo culture" or "organ culture," which will be described later, may be added.

After being transplanted to a fetus separated from a pregnant mammalian host (uterus), the manufactured mesenchymal stem cells or kidney stem cells may be matured in the fetal body using whole embryo culture to contribute to formation of early stage kidney suitable for transplantation, and then further cultured using organ culture. In addition, the kidney for transplantation may be transplanted to the greater omentum or the like of a mammal such as a human.

A time for transplanting the manufactured mesenchymal stem cells or kidney stem cells to the fetus can be suitably adjusted. In an experiment using rats, rats at embryonic day 9 to 12, for example day 10 to 12, for example day 10 to 11.5 were preferable. For large mammals including pigs, embryos at a similar stage to the above stage may also be suitably used. In addition, embryos at stages before and after the above stage can also be used by selecting conditions. It is important that, at least at the time of transplantation, a host immune system is still in the stage of immune tolerance.

The host immune system is not sufficiently developed at this stage of the whole embryo culture. Therefore, the host immune system has a tolerance to heterologous cells. Using an intrinsic growth system of the immune-defenseless heterologous host, a self organ is generated from its own mesenchymal stem cells.

As a site of a fetus to which mesenchymal stem cells or kidney stem cells are transplanted is set as an organ-generated site, an organ for transplantation can be suitably manufactured. For this reason, while it is necessary to execute the transplantation at the time at which the site is determined as an organ-generating site, it is preferable that blast cells of a kidney be in a sprouting stage before development. For example, the mesenchymal stem cells or kidney stem cells may be transplanted to a mesenchyme which forms metanephroi, thereby differentiating into mesangium cells, urine capillary epithelial cells and glomerular epithelial cells, and the mesenchymal stem cells or kidney stem cells are transplanted to the intermediate mesoderm, thereby differentiating into a ureteric bud-derived collecting duct and a ureter.

Here, the whole embryo culture will be described. The whole embryo culture is performed when mesenchymal stem cells or kidney stem cells are transplanted to a fetus separated from a pregnant mammalian host (uterus). After the uterus is separated from a parent body, the mesenchymal stem cells or kidney stem cells are transplanted to a fetus separated from an outer layer including the uterus membrane, the decidua and the Reichert's membrane, and then cultured in a culture bottle for the whole embryo culture.

More specifically, for example, the uterus is extracted from a parent body under anesthesia using a stereomicroscope, etc. Embryos of the rat at embryonic day 9 to 12, for example day 10 to 12, for example day 10 to 11.5, for example day 11.5 are dissected from the outer layer including the uterus membrane, the decidua and the Reichert's membrane. Further, the yolk sac and amniotic membrane are opened to inject mesenchymal stem cells or kidney stem cells thereinto, and the chorion, the allantoic membrane and the placenta still remain. Embryos identified as having undergone the successful injection of the mesenchymal stem cells or kidney stem cells are cultured in a culture bottle in which 3 mL of a culture medium (glucose, penicillin B, streptomycin and amphotericin B) is added to a centrifuged rat serum.

The culture bottle is rotated using, for example, an incubator (trade name "RKI 10-0310," Ikemoto, Inc.). A culture time may be, for example, 12 to 60 hours, for example, 24 to 48 hours, or for example, 48 hours. After a predetermined culture time, the resulting product is morphologically and functionally evaluated to determine an anlagen of the kidney for transplantation. The anlagen is separated from the fetus, and may be subjected to organ culture as will be described later.

Subsequently, the organ culture will be described. The anlagen is placed on a filter, and a medium such as DMEM is added to an underlying culture dish. In addition, the culture dish was put into a 5% $CO_2$ incubator for culture. A culture time may be, for example, 12 to 168 hours, for example, 18 to 72 hours, for example, 24 to 48 hours, or for example, 24 hours. For example, the cultured product may be transplanted to the greater omentum at the time of approximately 24 hours. A culture temperature may be, for example 20 to 45° C., for example, 25 to 40° C., or for example, 37° C.

Subsequently, relay culture will be described. The relay culture refers to the whole embryo culture being performed for 2 to 60 hours, and then the organ culture being performed for 12 to 168 hours. In addition, after the organ culture, the cultured product may be transplanted to the greater omentum of an animal.

The size of the organ is the same as that of a host animal's own organ. Therefore, for example, to form a kidney capable of sufficiently exhibiting its function for a human, the host animal may be a mammal having organs of a similar size to those of a human. However, if the organ is a kidney, it is not necessary that it be the same size, and as long as it has one tenth of the kidney function, dialysis can be sufficiently performed and a life can be sufficiently maintained. For this reason, it is determined that the optimal host is a pig, and the host size is sufficient at the organ size of a miniature pig. Further, in the case of a pig, it is difficult to perform whole embryo culture, and thus an organ for transplantation in which mesenchymal stem cells or kidney stem cells are injected into the organ-generating site of a fetus is manufactured by manipulation in the uterus.

The organ for transplantation manufactured as described above is dissected from a host identified in its function, and provided to a recipient. After transplantation, the organ for transplantation is continuously grown in vivo, and thus the formation of a replicated kidney exhibiting a kidney function is completed.

Transplantation of a kidney for transplantation to the greater omentum or abdominal aorta of a mammal such as a human can be performed by general surgical treatment. For example, a method of picking tissue to be transplanted with a sharp forceps, creating a slightly-cut opening on the surface of adipose tissue of the greater omentum with a tip of the forceps and implanting the tissue into the opening is used. In addition, the transplantation can be performed on the greater omentum or abdominal aorta using an endoscope.

There are both mesenchymal stem cells and kidney stem cell-derived cells and host animal-derived cells in the formed kidney. The mixed host-derived cells may cause immune rejection when the kidney is transplanted to a recipient. Here, after the kidney formation, it is necessary to completely remove the host-derived cells.

To prevent a host-derived antigenic substance from being mixed in the formed kidney, for example, a method of regulatively manufacturing a potential host animal capable of inducing programmed cell death and manufacturing a kidney using the animal as a host is used. As mesenchymal stem cells or kidney stem cells are transplanted to a corresponding site of an embryo of the host animal to manufacture a kidney, and then cell death is host-specifically induced, the host-derived cells can be completely eliminated before the transplant to a recipient.

Theoretically, for example, iPS cells manufactured from a patient's own cells are differentiated, and mesenchymal stem cells or kidney stem cells are prepared and then applied in the above-described method, thereby manufacturing a regenerated kidney derived from the patient's own cells.

[Organ Structure]

In the first embodiment, the present invention provides an organ structure in which a kidney, a first ureter, a first urinary bladder, a second ureter, and a second urinary bladder are sequentially connected in this order.

FIG. 1 is a diagram of an organ structure according to an embodiment. As shown in FIG. 1, when an organ for transplantation having a kidney 110, a first ureter 120 and a first urinary bladder 130 is transplanted to a host, the organ is grown in vivo, and thus urine is produced. Here, as shown in FIG. 1 and an experimental example which will be described later, a urinary bladder 130 (first urinary bladder) of the organ for transplantation is connected with a ureter 140 (second ureter) of the host, which is extended to a urinary bladder 150 (second urinary bladder) of the host, and the transplanted kidney 110 can transfer the produced urine to the urinary bladder 150 of the host. In other words, according to the organ transplantation, the produced urine may be excreted from the regenerated kidney which is transplanted. This is considered to be caused by peristalsis of the first ureter 120 and the second ureter 140.

The organ for transplantation may be transplanted to, for example, the greater omentum or abdominal aorta of the host, or may be transplanted to, for example, the spleen (near the splenic artery) of the host.

In the organ structure of the embodiment, the kidney, the first ureter and the first urinary bladder correspond to the above-described organ for transplantation. An animal from which the kidney, the first ureter and the first urinary bladder (organ for transplantation) are derived may be different from that (host, transplantation target) from which the second ureter and the second urinary bladder are derived. For example, a pig-derived organ for transplantation can be transplanted to a human or a cat to form an organ structure. This is one of the options that can be made when there is a lack of kidneys for transplantation.

In the organ structure of the embodiment, the kidney, the first ureter and the first urinary bladder may be derived from a genetically-manipulated non-human animal which is different from a transplantation target. For example, when being transplanted to a human or cat, the kidney, the first ureter and the first urinary bladder may be derived from a pig genetically manipulated to reduce rejection.

In the organ structure of the embodiment, the kidney, the first ureter and the first urinary bladder are preferably substantially composed of human cells, and most preferably are composed of a patient's own cells. Here, the meaning of "substantially" is as described above.

The kidney, the first ureter and the first urinary bladder may be prepared by injecting human stem cells into, for example, a genetically manipulated porcine fetus. In addition, the animal from which the second ureter and the second urinary bladder are derived may be, for example, a human or a cat.

[Treatment Methods]

In the first embodiment, the present invention provides a method of transplanting a kidney, which includes (a) a process of transplanting an organ for transplantation having a kidney, a ureter and a urinary bladder to a patient or a diseased animal, and (b) a process of connecting the urinary bladder of the organ for transplantation with a ureter of the patient or the diseased animal after a predetermined period of the transplantation. The patient or diseased animal is, for example, a human, a cat or the like.

The method in the embodiment may be a method of treating a kidney disease. As an organ for transplantation, that described above may be used.

The organ for transplantation transplanted in the process (a) is left for a predetermined period to grow, and urine production is initiated. The predetermined period may be a period for sufficiently growing the organ for transplantation until hydronephrosis occurs. The predetermined period is suitably adjusted according to symptoms of a patient or diseased animal, and for example, is 1 to 10 weeks.

Subsequently, the process (b) is performed in the predetermined period after transplantation. In the process (b), the urinary bladder of the organ for transplantation is connected with the ureter of a patient or diseased animal. Here, the ureter of the patient or diseased animal is connected to the urinary bladder of the patient or diseased animal.

As the urinary bladder of the organ for transplantation or the urinary bladder of the patient or diseased animal is connected with the ureter of the patient or diseased animal, urine produced by the organ for transplantation can be excreted to the urinary bladder of the patient or diseased animal. More specifically, urine produced by the kidney of the organ for transplantation is excreted to the urinary bladder of the organ for transplantation through the ureter of the organ for transplantation, and then excreted from the urinary bladder of the organ for transplantation to the urinary bladder of the patient or diseased animal through the ureter of the patient or diseased animal.

According to the method in the embodiment, the urine produced by the kidney of the organ for transplantation can be excreted to the urinary bladder of the patient or diseased animal.

EXAMPLES

The present invention will be described in further detail with reference to the following experimental examples, but is not limited to the experimental examples.

Experimental Example 1

(Transplantation of Kidney to Pig and Analysis of Transplanted Kidney)

Figure 2B:
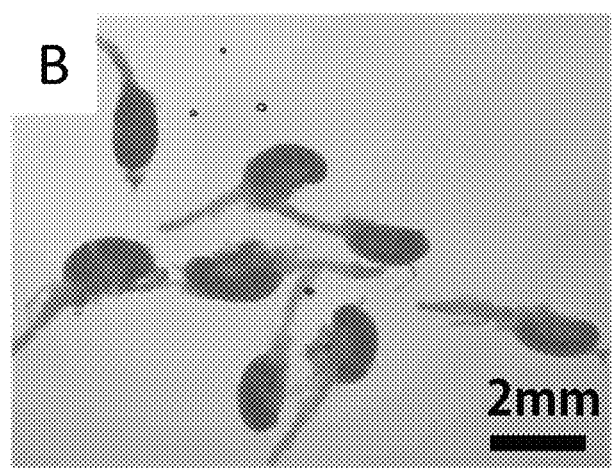
FIG. 2B is an image of extracted porcine metanephroi.
Figure 2C:
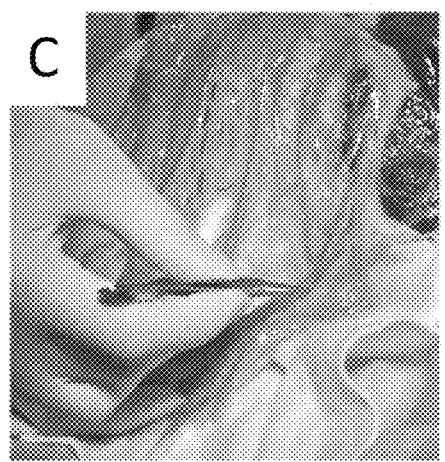
FIG. 2C is an image illustrating the transplantation of the metanephroi to the greater omenta.

A cloned pig was manufactured using a somatic cell cloning technique. After that, fetuses at embryonic day 30 were extracted from the cloned pig, and porcine metanephroi (which can, hereinafter, be referred to as "MN") were extracted under a microscope. FIG. 2A is an image of the cloned porcine fetuses at embryonic day 30. FIG. 2B is an image of the extracted porcine MN. Subsequently, the extracted MN were transplanted to the greater omenta of syngeneic pigs. FIG. 2C is an image illustrating the transplanted state. Three, five and eight weeks after the transplantation of the MN to the greater omenta, the pigs were sacrificed under isoflurane anesthesia, and the transplanted MN were extracted and analyzed.

Figure 3:
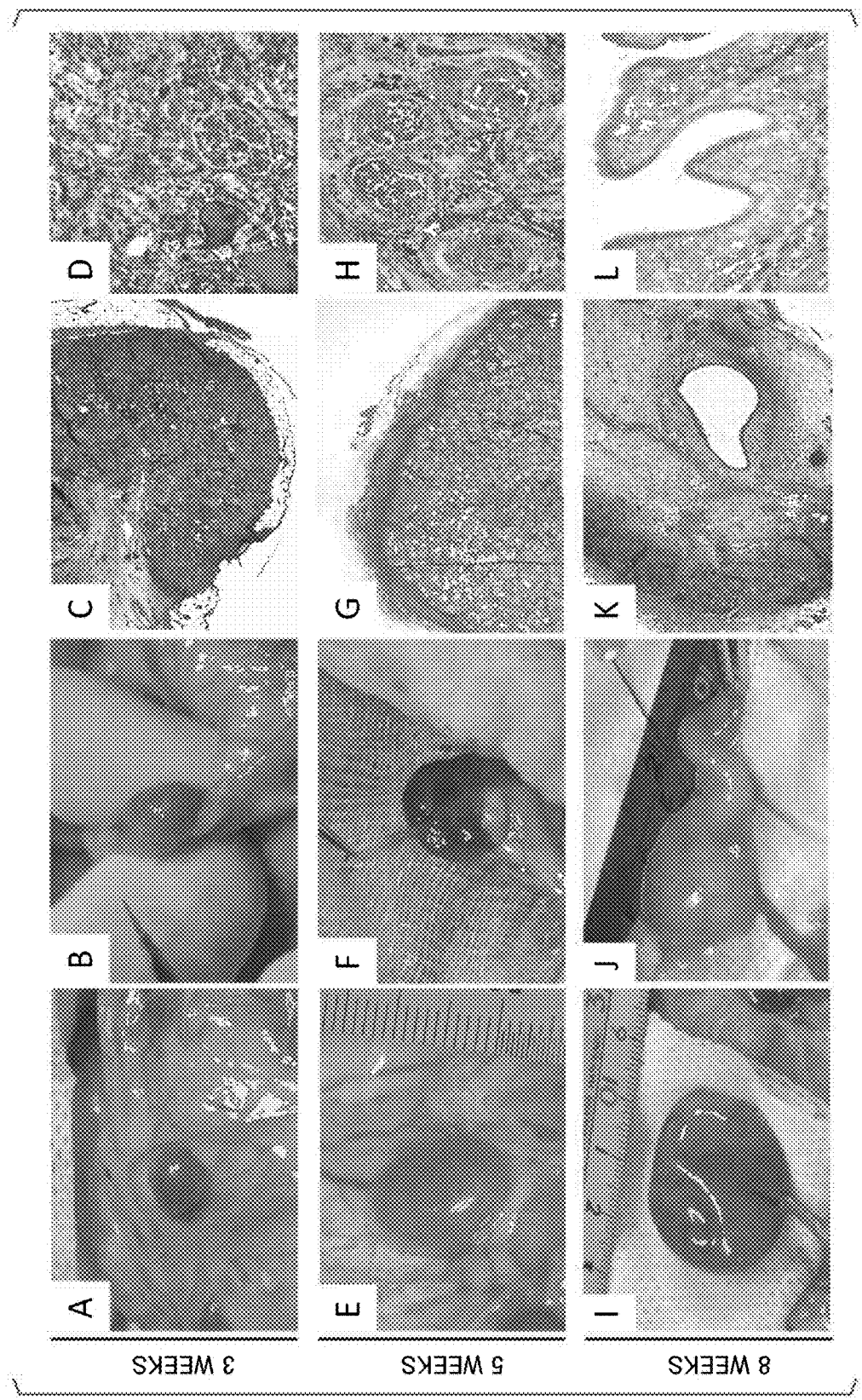
FIG. 3A to L are images of the metanephroi which are transplanted to pigs.

FIGS. 3A to 3L are images of the transplanted MN. As shown in FIGS. 3A and 3B, the transplanted MN were well grown to have a major axis of approximately 5 to 7 mm three weeks after the transplantation. In addition, as shown in FIGS. 3C and 3D, according to the histological analysis by Masson trichrome staining, it was identified that a glomerular or renal tubular structure was formed.

Figure 5:
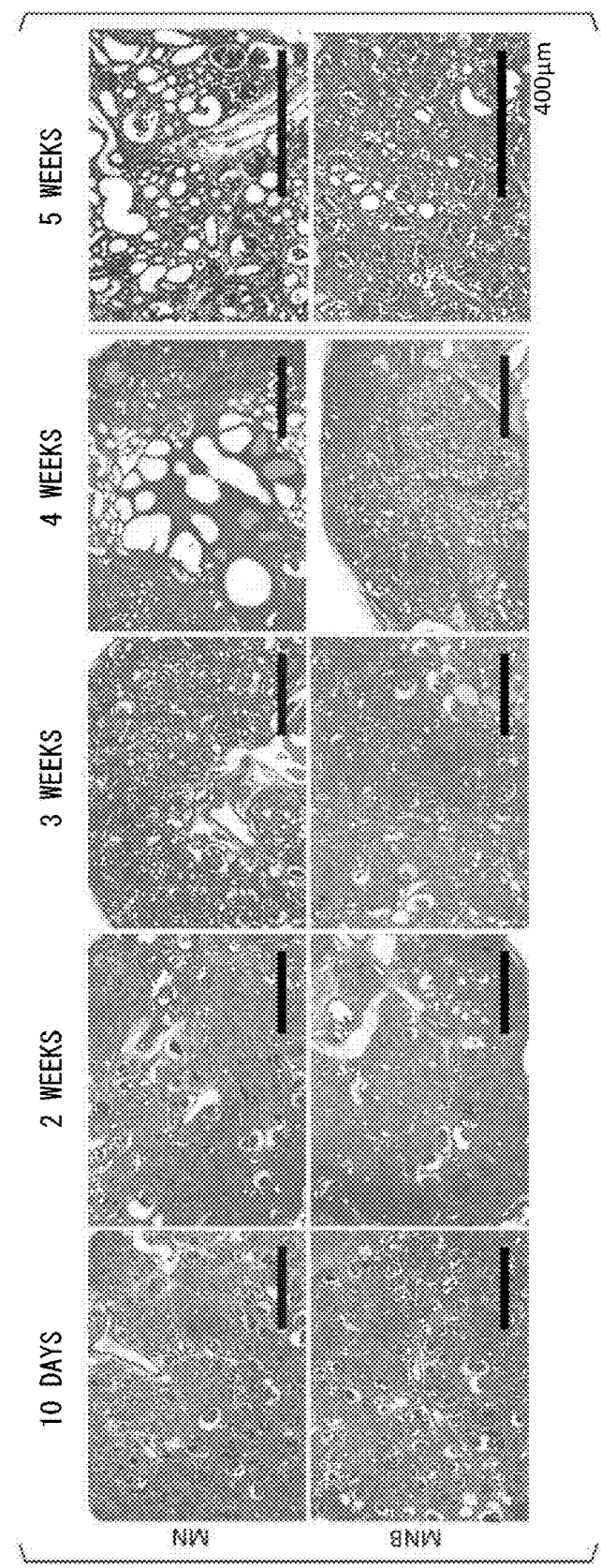
FIG. 5 is an image illustrating results of histological analysis by Masson trichrome staining for the transplanted metanephroi in the MN groups and MNB groups in Experimental Example 2.

In addition, as shown in FIGS. 3E and 3F, 5 weeks after transplantation, the major axes of the metanephroi exceeded 10 mm, and the growth of a ureter and storage of urine in the ureter were also confirmed. Invasion of blood vessels from a host pig into the kidney after transplantation was also confirmed. In addition, as shown in FIGS. 3G and 3H, as in the third week, kidney tissue structures such as glomerular and renal tubules, etc. were maintained, and stromal bleeding and congestion were histologically observed.

Figure 8:
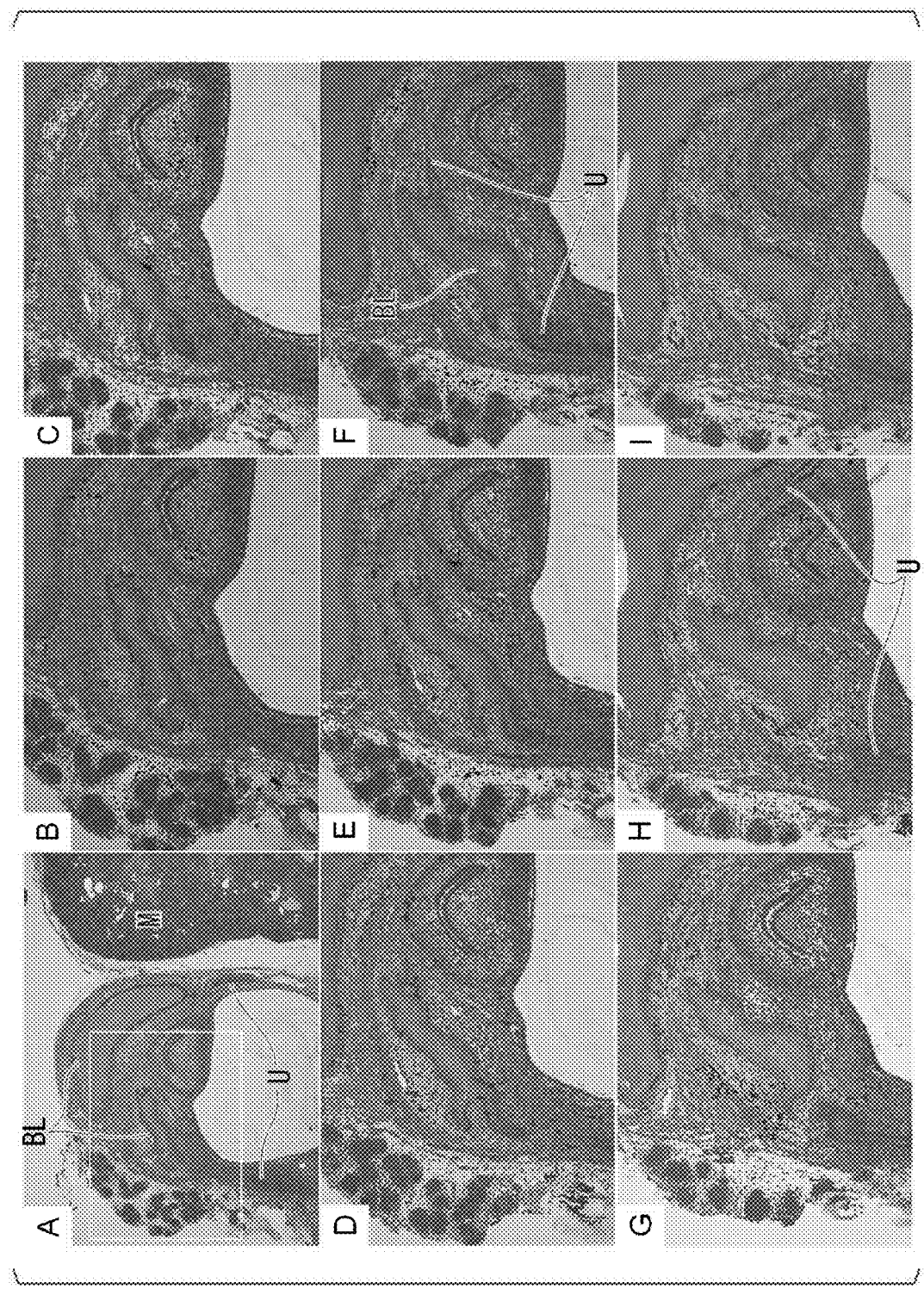
FIG. 8A to I are images illustrating histological analysis results obtained by Masson trichrome staining on serial sections of a ureteropelvic junction of the metanephros of the MNB group in Experimental Example 2.

Further, as shown in FIG. 3I, 8 weeks after the transplantation, the metanephroi were further grown to have a major axis of approximately 4 cm, but it was visually identified that renal parenchyma was thin and showed hydronephrosis. In addition, as shown in FIG. 3J, the expansion of a metanephros ureter was identified. As shown in FIG. 3K, it was histologically observed that the metanephros cortex was reduced, which resulted in stromal fibrosis. However, as shown in FIG. 3L, after transplantation, the ureter epithelium of a metanephros was relatively maintained.

From the results described above, although the metanephroi of the cloned pig can become larger, to continue the growth of metanephroi, the construction of an excretory tract for urine produced by the metanephroi is considered to be required.

Experimental Example 2

(Kidney Transplantation to Rat and Analysis of Transplanted Kidney)

Figure 4A:
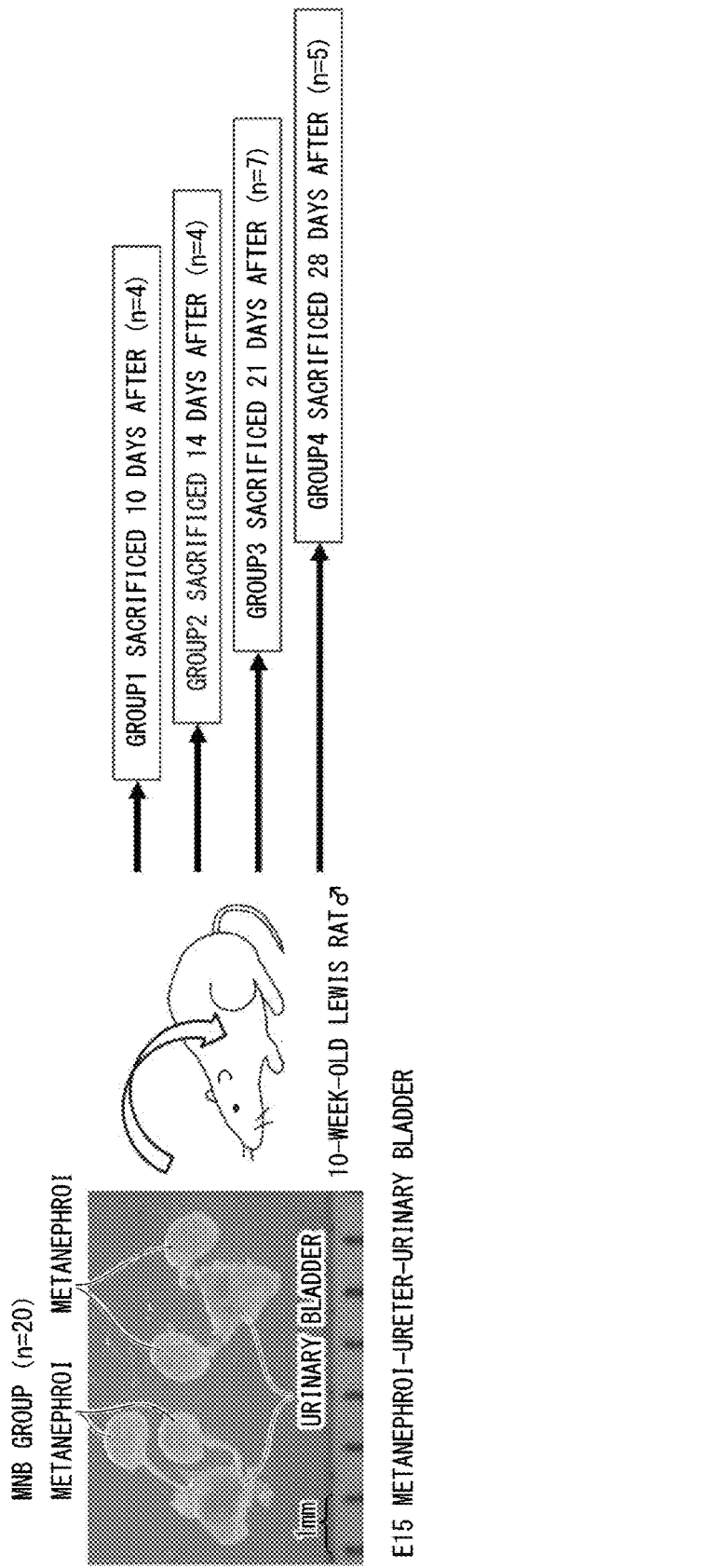
FIG. 4A is a diagram illustrating the experimental schemes for MNB groups 1 to 4 (groups in which metanephroi-urodeum were transplanted (organ for transplantation having a kidney, a ureter and a urinary bladder)) in Experimental Example 2.
Figure 4B:
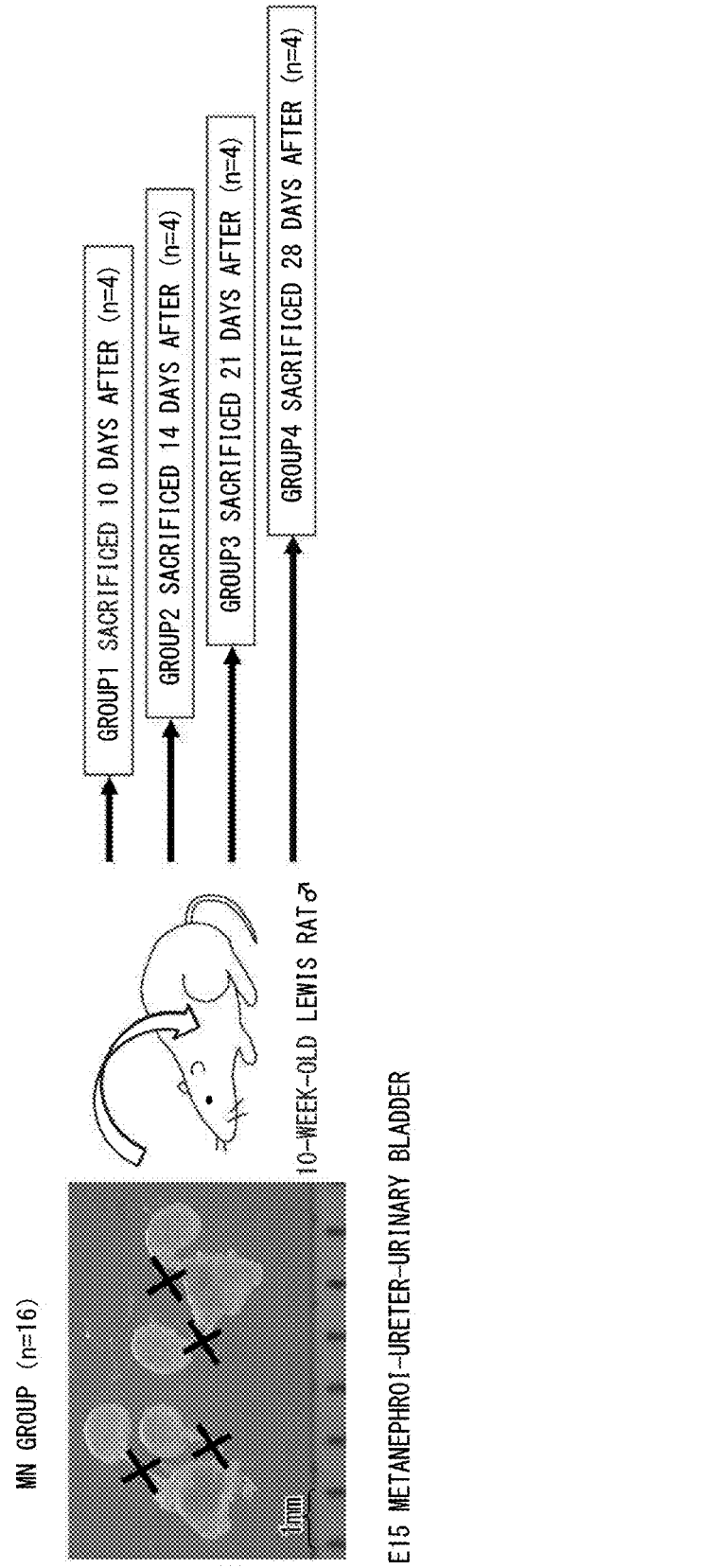
FIG. 4B is a diagram illustrating the experimental schemes for MN groups 1 to 4 (groups in which only metanephroi were transplanted) in Experimental Example 2.

FIGS. 4A and 4B are images illustrating an experimental scheme. As host rats to which kidneys are transplanted, 10-week-old Lewis rats (Sankyo Labor Service Co., Ltd. or Nippon Clea Co., Ltd.) were used.

As shown in the image of FIG. 4A, metanephroi with urinary bladders extracted from murine fetuses at embryonic day 15, that is, organs (which may, hereinafter, be called "cloaca (CL)") having a kidney, a ureter and a urinary bladder were transplanted to paraaortic regions of the rats of MNB groups 1 to 4 grouped as shown in FIG. 4A.

In addition, as shown in the image of FIG. 4B, urinary bladders and metanephroi which were extracted from porcine fetuses at embryonic day 15 were transplanted to the paraaortic regions of rats in MN groups 1 to 4 grouped as shown in FIG. 4B after ureters were cut.

Subsequently, 10 days (group 1), 14 days (group 2), 21 days (group 3) and 28 days (group 4) after the transplantation, the rats of the MNB and MN groups were sacrificed, and the transplanted organ was extracted and analyzed.

FIGS. 5, 6A to 6D and 7A to 7D are images illustrating analysis results. FIG. 5 is an image illustrating histological analysis results by Masson trichrome staining on the transplanted metanephroi in MN and MNB groups. The black line in the drawing is 400 μm. In the MN group, after growth progressed, renal tubular expansion was identified. In addition, 4 weeks after the transplantation, the number of glomeruli was small.

FIGS. 6A to 6D and FIGS. 7A to 7D are graphs or images illustrating the measurement results of a graft weight, a ratio of renal tubular expansion, a percentage of a fibrosis area, the number of glomeruli, urine capacity, an amount of creatinine, and a urea nitrogen amount. The measurement results are represented in mean±standard deviation. Statistical analysis was performed with software (trade name "GraphPad Prism 5," GraphPad Software, Inc.). The difference in averages between two specimens was determined by independent t-test. Multiple comparison of three groups or more was analyzed by ANOVA.

Figure 6A:
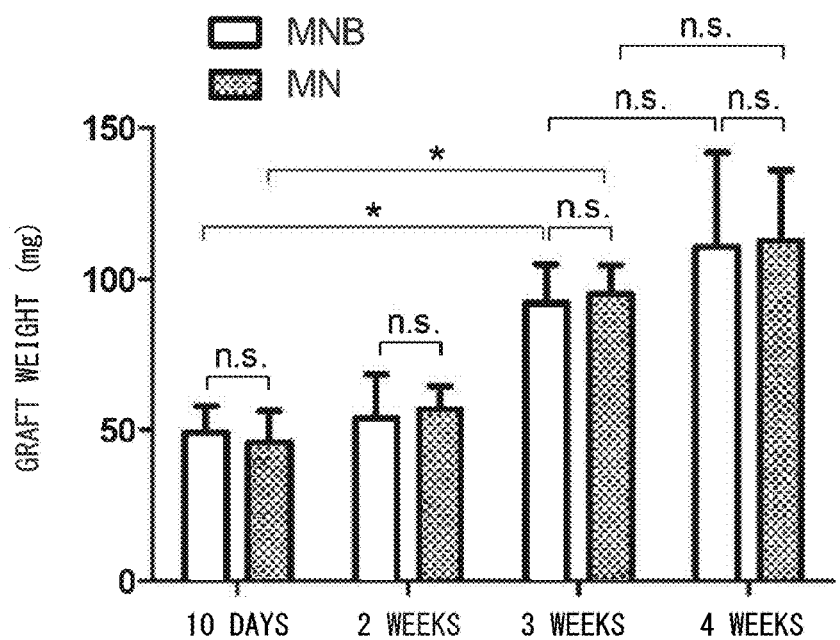
FIG. 6A is a graph illustrating an analysis result of pathological findings on the transplanted metanephroi in Experimental Example 2.

As shown in FIG. 6A, graft weights of the MNB and MN groups increased up to 2 to 3 weeks after the transplantation, and began to level off within 3 to 4 weeks after the transplantation. In addition, a significant difference in growth weights between the MNB and MN groups was not observed.

Figure 6B:
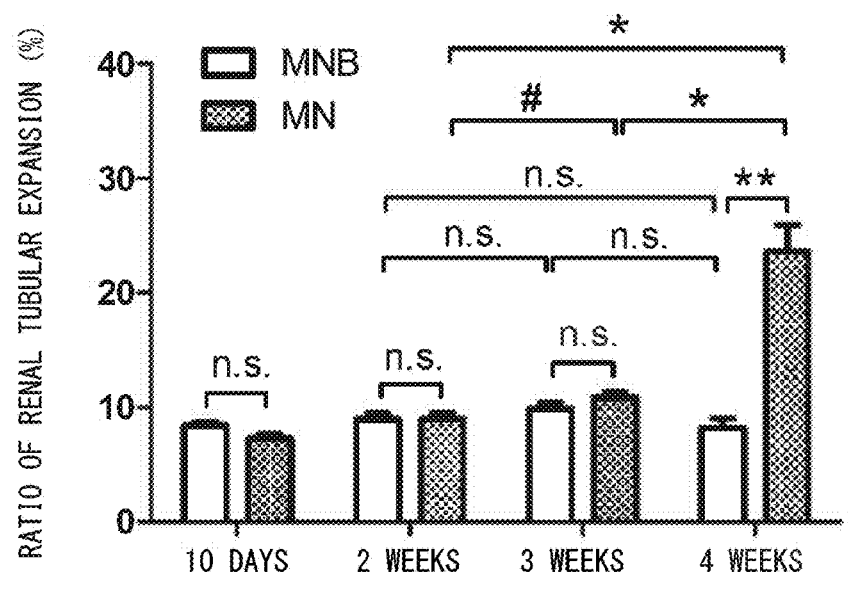
FIG. 6B is a graph illustrating an analysis result of pathological findings on the transplanted metanephroi in Experimental Example 2.
Figure 6C:
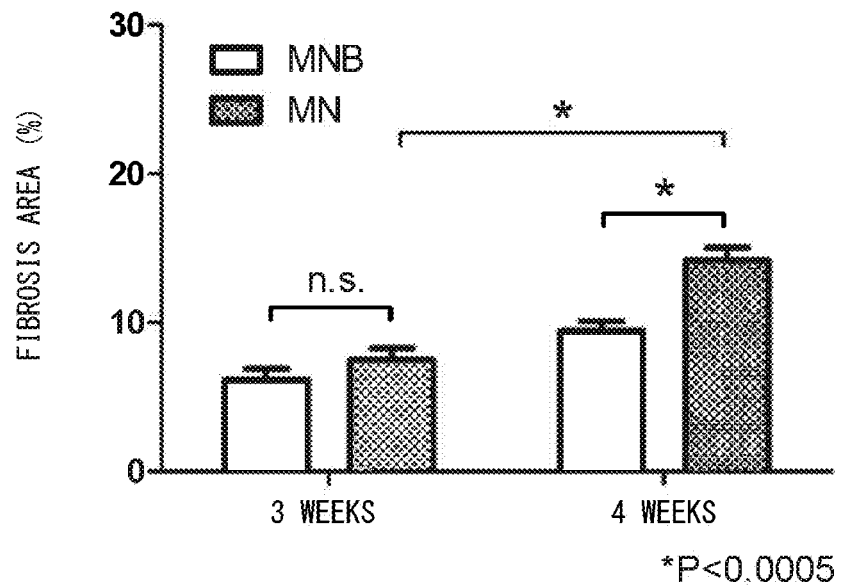
FIG. 6C is a graph illustrating an analysis result of pathological findings on the transplanted metanephroi in Experimental Example 2.

However, as shown in FIG. 6B, in the MN group, renal tubular expansion was shown in the third week after the transplantation ($P<0.05$), and a further increase was identified within 4 weeks after the transplantation ($P<0.0005$). In contrast, in the MNB group, the progression of renal tubular expansion was not identified, and 4 weeks after the transplantation, the MN group showed significantly further renal tubular expansion than the MNB group ($P<0.0001$), and as shown in FIG. 6C, stromal fibrosis also progressed ($P<0.0005$). Further, a proportion of the renal tubular expansion and a proportion of the stromal fibrosis were quantified with software (trade name "MetaVue", Modular Devices Corp.).

Figure 6D:
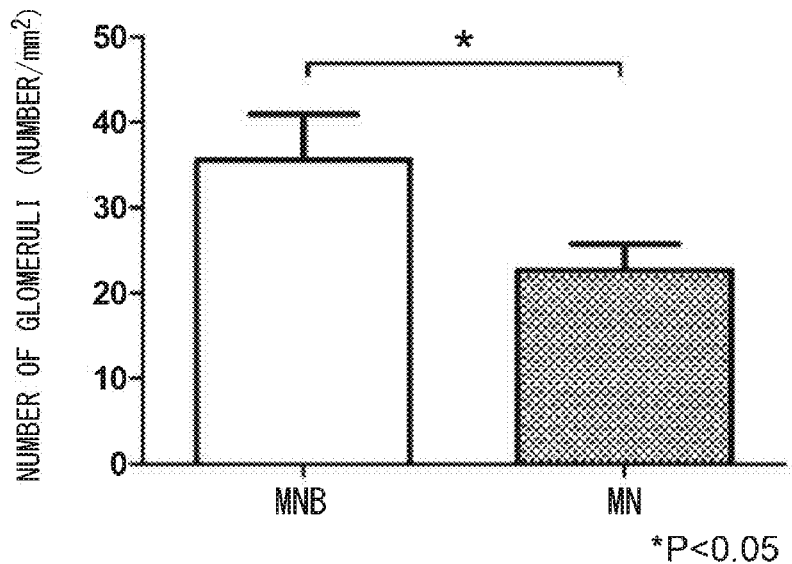
FIG. 6D is a graph illustrating an analysis result of pathological findings on the transplanted metanephroi in Experimental Example 2.

In addition, as shown in FIG. 6D, the number of glomeruli per unit area of the metanephros in the fourth week after the transplantation significantly increased in the MNB group ($P<0.05$).

Figure 7A:
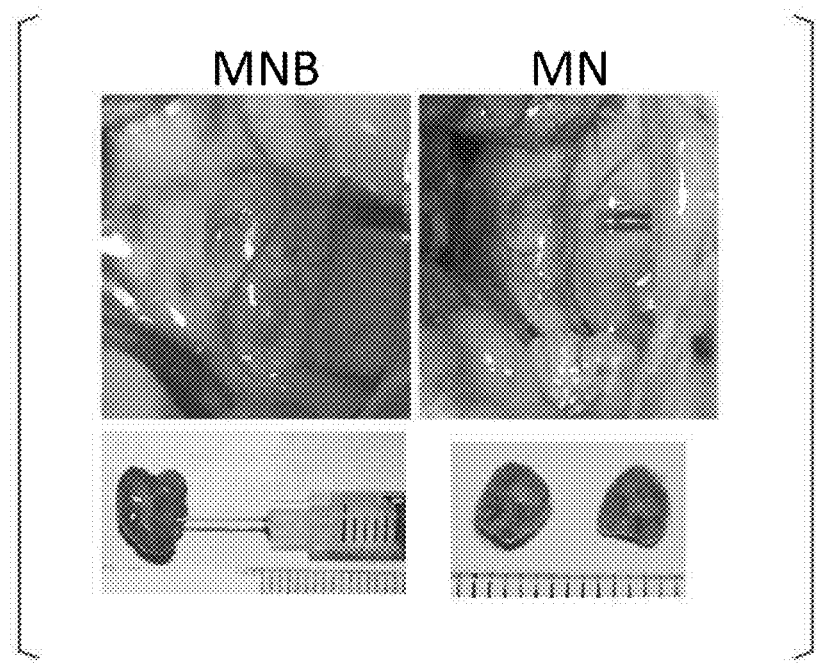
FIG. 7A shows images illustrating an analysis result of acquired renal function for the transplanted metanephroi in Experimental Example 2.
Figure 7B:
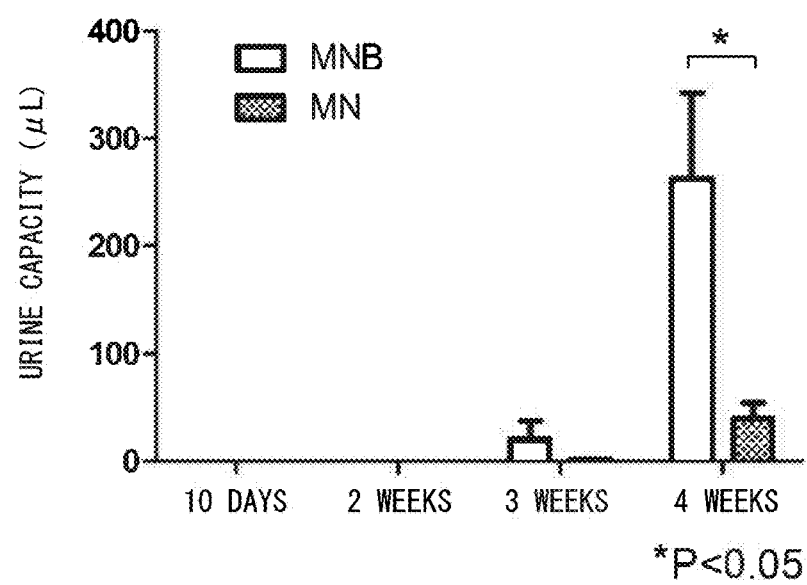
FIG. 7B is a graph illustrating an analysis result of acquired renal function for the transplanted metanephroi in Experimental Example 2.
Figure 7C:
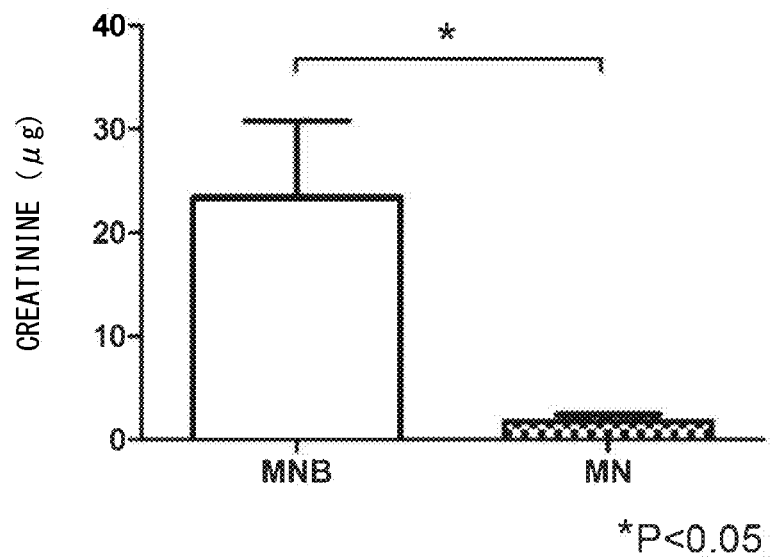
FIG. 7C is a graph illustrating an analysis result of acquired renal function for the transplanted metanephroi in Experimental Example 2.
Figure 7D:
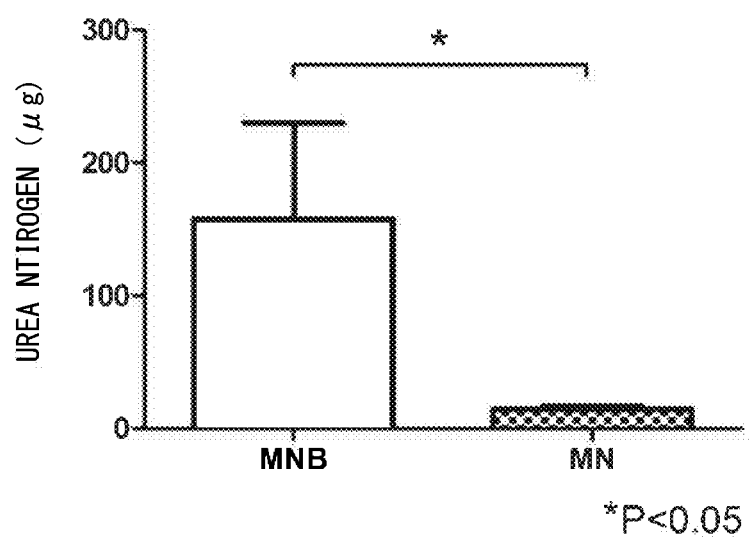
FIG. 7D is a graph illustrating an analysis result of acquired renal function for the transplanted metanephroi in Experimental Example 2.

In addition, as shown in FIGS. 7A and 7B, in the MNB group, from 3 weeks after the transplantation, urine was stored in a urinary bladder of the metanephroi, and in the fourth week after the transplantation, an accumulative amount of urine in the urinary bladder significantly increased, compared to that in the MN group ($P<0.05$). Further, as shown in FIG. 7C, an excretion amount of creatinine in urine significantly increased in the MNB group ($P<0.05$), and as shown in FIG. 7D, an excretion amount of urea nitrogen in urine significantly increased in the MNB group ($P<0.05$).

The results described above show that the metanephros transplantation with a urinary bladder further inhibited hydronephrosis and stromal fibrosis, which occur with the growth of the transplanted metanephroi, and thus was superior to transplantation of only metanephroi.

FIGS. 8A to 8I are images illustrating histological analysis results obtained by Masson trichrome staining on serial sections of a ureteropelvic junction of the metanephros of the MNB group. In the drawings, BL represents a CL urinary bladder, U represents a CL ureter, and M represents a metanephros. From the above results, it was revealed that the ureterovesical junctions of the transplanted metanephroi in the MNB group were sufficiently grown.

The difference in growth of the transplanted metanephroi in the MNB group and MN group was considered to be due to the functions of the ureter and the urinary bladder.

Experimental Example 3

(Construction of Urinary Excretory Tract of Rat)

A metanephros with a urinary bladder, that is, an organ (CL) having a kidney, a ureter and a urinary bladder was extracted from a murine fetus at embryonic day 15, and then transplanted to a paraaortic region of the rat. Subsequently, 4 weeks after the transplantation, the left kidney of the host rat was extracted, and then a surgical anastomosis between the transplanted urinary bladder of the metanephros (CL urinary bladder) and a left ureter of the host rat was performed under a microscope.

Three to four weeks after the surgery, the rat was opened to cut the host ureter connected with the CL urinary bladder through anastomosis, and it was confirmed that urine produced from the grown metanephros was continuously excreted through the host ureter.

Figure 9:
FIG. 9A is an image illustrating a contrast CT result for Experimental Example 3.
FIG. 9B is an image illustrating visible findings on the same part as used above in Experimental Example 3.

The urinary excretion was analyzed by X-ray computed tomography (CT) on a different rat subjected to the same treatment. FIG. 9A is an image illustrating the X-ray CT result. In the drawing, M represents a transplanted metanephros, and BL represents a CL urinary bladder. From the result of intravenous urography by X-ray CT, 10 minutes after the administration of a contrast medium (Omnipark, Daiichi Sankyo Co.), accumulation of the contrast media in the urinary bladder (CL urinary bladder) of the transplanted metanephros was identified. In addition, with the passage of time, excretion of the contrast media to the urinary bladder of the host through the ureter of the host was identified.

FIG. 9B is an image illustrating visible findings on the same part. M represents transplanted metanephroi, BL represents a CL urinary bladder, and U represents a host ureter.

Figure 10:
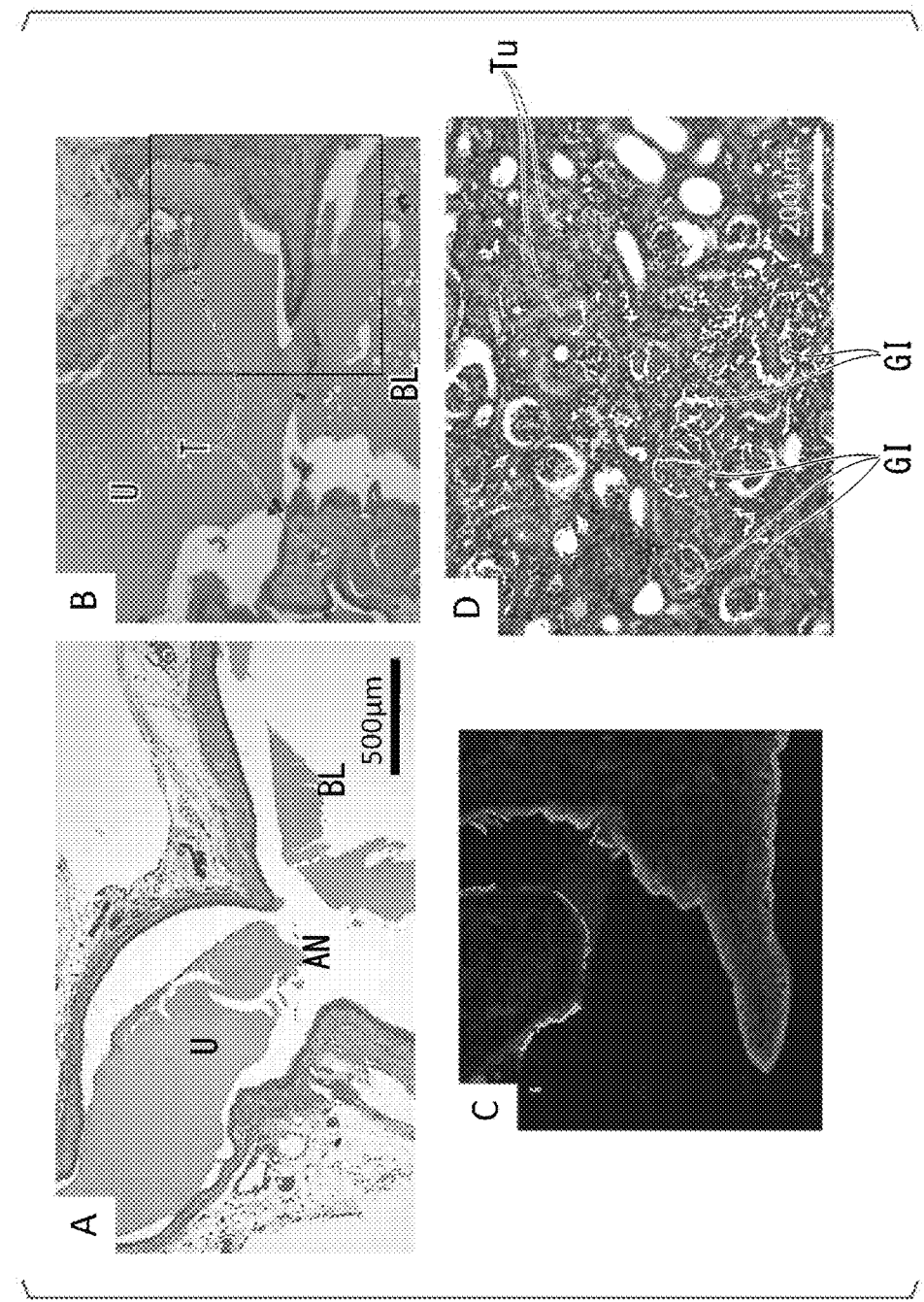
FIG. 10A to D are images illustrating histological analysis results of a ureterovesical anastomotic region in Experimental Example 3.

FIGS. 10A to 10D are images illustrating histological analysis results of a ureterovesical anastomotic region. As shown in FIGS. 10A and 10B, in the histological examination of the ureterovesical anastomotic region using hematoxylin-eosin (HE) staining, the ureterovesical anastomotic region was a sufficient opening. In these drawings, U represents a host ureter, AN represents a ureterovesical anastomotic region, BL represents a CL urinary bladder, and T represents a suture.

In addition, as shown in FIG. 10C, as a result of immunostaining for transitional epithelial cells of a urinary tract with goat anti-UPK III polyclonal antibody (sc-15182, Santa Cruz Biotechnology), anastomosis between transitional epitheliums was identified. From the above-described results, it was identified that the ureter of the host was tightly connected with the urinary bladder (CL urinary bladder) of the metanephros by anastomosis.

In addition, as shown in FIG. 10D, 7 to 8 weeks after the metanephros transplantation, and the rat was sacrificed, kidney structures such as glomerular and renal tubules, etc. were maintained in the transplanted metanephros. In the drawing, GI represents the glomerulus, and Tu represents the renal tubule.

Figure 11A:
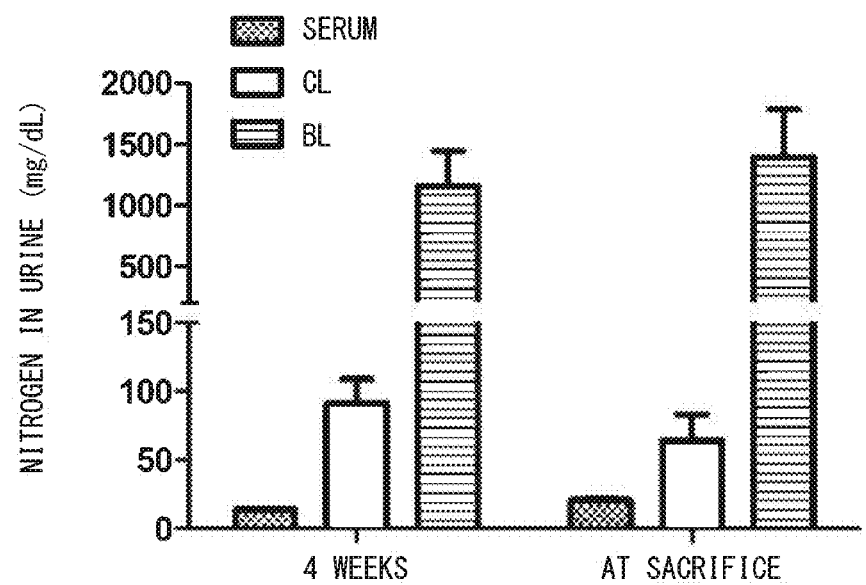
FIG. 11A shows a result obtained by measuring urea nitrogen concentrations in a serum of a host rat, urine (CL) in a CL urinary bladder excreted from a transplanted metanephros, and urine (BL) in a urinary bladder of the host in Experimental Example 3.

FIG. 11A shows a result obtained by measuring nitrogen concentrations in a serum of a host rat, urine (CL) in a CL urinary bladder excreted from a transplanted metanephros, and urine (BL) in a urinary bladder of the host.

Figure 11B:
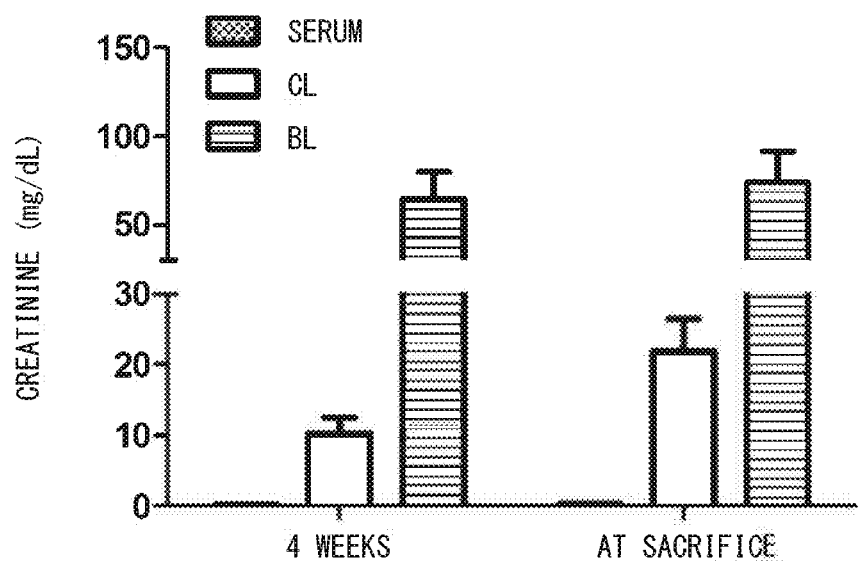
FIG. 11B shows a result obtained by measuring creatinine concentrations in a serum of a host rat, urine (CL) in a CL urinary bladder excreted from a transplanted metanephros, and urine (BL) in a urinary bladder of the host in Experimental Example 3.

In addition, FIG. 11B shows a result obtained by measuring creatinine concentrations in a serum of a host rat, urine (CL) in a CL urinary bladder excreted from a transplanted metanephros, and urine (BL) in a urinary bladder of the host.

From these results, it was shown that the urine in the CL urinary bladder has higher concentrations of urea nitrogen and creatinine than those in a serum of the host rat, and the transplanted metanephros has a kidney function of producing urine by filtrating the blood of the host rat.

From the above-described results, it was concluded that, by using a system (which may, hereinafter, be called a "step-wise peristalic ureter (SWPU) system") for connecting the urinary bladder of an organ for transplantation having a kidney, a ureter and a urinary bladder with a host ureter, urine produced by the transplanted metanephros may be allowed to be continuously excreted into the host urinary bladder through the host ureter, and thus it is possible to construct a urinary excretory tract of a regenerated kidney, which has been difficult until now.

Experimental Example 4

(Transplantation of Kidney with Urinary Bladder to Pig and Analysis of Transplanted Kidney)

Figure 12:
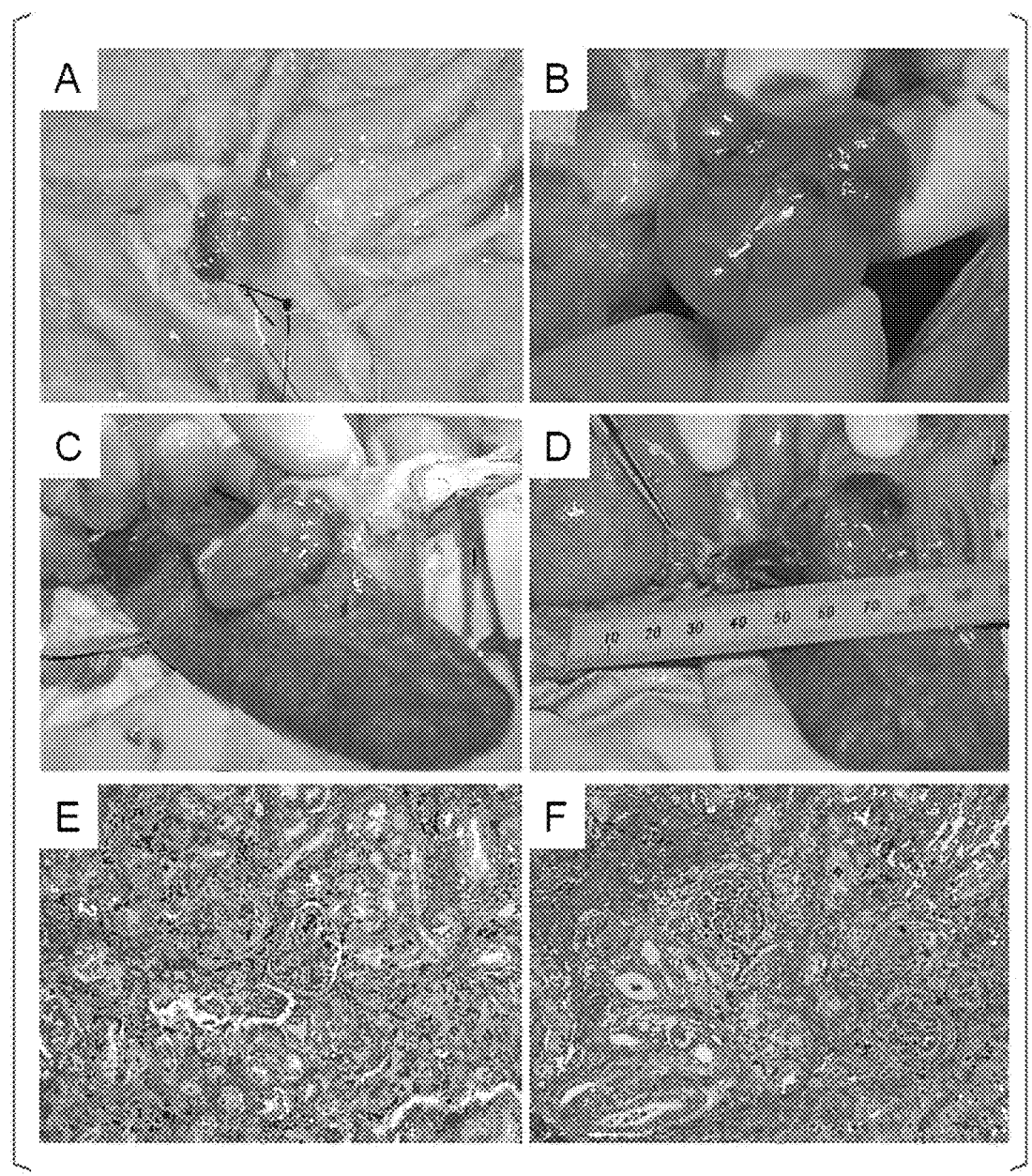
FIGS. 12A and B are images illustrating results of Experimental Example 4. C to F are images illustrating results of Experimental Example 5.

From a porcine fetus at embryonic day 30, a metanephros with a urinary bladder, that is, an organ (CL) having a kidney, a ureter and a urinary bladder was extracted, and transplanted to the greater omentum of a syngeneic pig. As shown in FIG. 12A, the transplanted metanephros with the urinary bladder was steadily grown as in the experiments for rats, and produced urine three weeks after the transplantation. In addition, as shown in FIG. 12B, in the fifth week after the transplantation, the metanephros became larger. It was identified that, in urine stored in the CL urinary bladder, urea nitrogen and creatinine were concentrated.

Experimental Example 5

(Construction of Urinary Excretory Tract of Pig)

A urinary excretory tract was constructed by an SPWU system using a cloned pig. From a porcine fetus at embryonic day 30, a metanephros with a urinary bladder, that is, an organ (CL) having a kidney, a ureter and a urinary bladder was extracted, and transplanted to the paraaortic and a peripheral regions of the splenic artery of the syngeneic pig.

As shown in FIG. 12C, it was shown that, 4 weeks after the transplantation, the metanephros was grown to less than 3 cm, and urine was stored in the CL urinary bladder.

Subsequently, as shown in FIG. 12D, the left kidney of the host pig was extracted, and a CL urinary bladder was connected with a host ureter by anastomosis.

Two weeks after the anastomosis, the host was sacrificed, and a difference in metanephros growth due to the absence or presence of ureter anastomosis was examined.

FIG. 12E is an image illustrating a histological analysis result of a CL metanephros connected with the host ureter by anastomosis. In addition, FIG. 12F is an image illustrating a histological analysis result of a CL metanephros which did not undergo ureter anastomosis. It was identified that the CL metanephros connected with the host ureter by anastomosis showed less stromal bleeding, renal tubular expansion, and sustainment of the renal tubular structure.

From the results described above, it was shown that the construction of a urinary excretory tract by the SPWU system using a cloned pig is useful in terms of the growth of a regenerated kidney to a large size and securing of the urinary excretory tract.

INDUSTRIAL ACCESSIBILITY

According to the present invention, an organ for transplantation which can produce urine and excrete the produced urine can be provided. In addition, an organ structure which can produce urine and excrete the produced urine can also be provided.

REFERENCE SIGNS LIST

110 Kidney
120 First ureter
130 First urinary bladder
140 Second ureter
150 Second urinary bladder

The invention claimed is:

1. An organ structure wherein a kidney, a first ureter, a first urinary bladder, a second ureter, and a second urinary bladder are sequentially connected in this order, wherein the first ureter, the first urinary bladder, the second ureter, and the second urinary bladder are derived from an animal.

2. The organ structure according to claim 1, wherein an animal species from which the kidney, the first ureter, and the first urinary bladder are derived is different from an animal species from which the second ureter and the second urinary bladder are derived.

3. The organ structure according to claim 1, wherein the animal from which the kidney, the first ureter, and the first urinary bladder are derived is a genetically-manipulated non-human animal.

4. The organ structure according to claim 1, wherein the animal from which the kidney, the first ureter, and the first urinary bladder are derived is a pig.

5. The organ structure according to claim 1, wherein the kidney, the first ureter, and the first urinary bladder are substantially composed of human cells.

6. The organ structure according to claim 1, wherein the animal from which the second ureter and the second urinary bladder are derived is a human.

7. The organ structure according to claim 1, wherein the animal from which the second ureter and the second urinary bladder are derived is a cat.

8. A method of producing the organ structure of claim 1, comprising:
    transplanting an organ having the kidney, the first ureter, and the first urinary bladder into a human, wherein the human has the second ureter and the second urinary bladder; and
    connecting the first urinary bladder to the second ureter of the human after a predetermined time period of the transplantation.

9. The method of claim 8, wherein each of the kidney, the first ureter, and the first urinary bladder is transplanted to the greater omentum or abdominal aorta of the human.

10. The method of claim 8, wherein each of the kidney, the first ureter, and the first urinary bladder is transplanted to the spleen of the human.

11. The method of claim 8, wherein the animal species from which the kidney, the first ureter, and the first urinary bladder are derived is different from an animal species from which the second ureter and the second urinary bladder are derived.

12. A method of producing the organ structure of claim 1, comprising:
    transplanting an organ having the kidney, the first ureter, and the first urinary bladder into a cat, wherein the cat has the second ureter and the second urinary bladder; and
    connecting the first urinary bladder to the second ureter of the cat after a predetermined time period of the transplantation.

13. The method of claim 12, wherein each of the kidney, the first ureter, and the first urinary bladder is transplanted to the greater omentum or abdominal aorta of the cat.

14. The method of claim 12, wherein each of the kidney, the first ureter, and the first urinary bladder is transplanted to the spleen of the cat.

15. The method of claim 12, wherein the animal species from which the kidney, the first ureter, and the first urinary bladder are derived is different from an animal species from which the second ureter and the second urinary bladder are derived.

* * * * *